US009678019B2

(12) United States Patent
Paul et al.

(10) Patent No.: US 9,678,019 B2
(45) Date of Patent: Jun. 13, 2017

(54) CHECK GRADER-ACTUATABLE INTERFACE FOR BOARD LUMBER SCANNING

(71) Applicant: Lucidyne Technologies, Inc., Corvallis, OR (US)

(72) Inventors: Aaron R. Paul, Corvallis, OR (US); Josh Miller, Corvallis, OR (US); Mark Miller, Albany, OR (US); Wendy Roberts, Albany, OR (US); Mark Hiatt, Corvallis, OR (US); Hayden Michael Aronson, Corvallis, OR (US)

(73) Assignee: Lucidyne Technologies, Inc., Corvallis, OR (US)

( * ) Notice: Subject to any disclaimer, the term of this patent is extended or adjusted under 35 U.S.C. 154(b) by 0 days.

(21) Appl. No.: 14/854,953

(22) Filed: Sep. 15, 2015

(65) Prior Publication Data

US 2017/0074805 A1 Mar. 16, 2017

(51) Int. Cl.

| | |
|---|---|
| ***G01N 21/89*** | (2006.01) |
| ***G06T 7/00*** | (2017.01) |
| ***G01N 21/88*** | (2006.01) |
| *G01N 21/84* | (2006.01) |

(52) U.S. Cl.

CPC ..... *G01N 21/8914* (2013.01); *G01N 21/8806* (2013.01); *G01N 21/8851* (2013.01); *G06T 7/0004* (2013.01); *G01N 2021/845* (2013.01); *G01N 2021/8854* (2013.01); *G06T 2207/10012* (2013.01); *G06T 2207/30161* (2013.01)

(58) Field of Classification Search

None

See application file for complete search history.

(56) References Cited

U.S. PATENT DOCUMENTS

| | | | | |
|---|---|---|---|---|
| 4,158,766 | A | 6/1979 | Sjödin | |
| 4,541,722 | A | 9/1985 | Jenks | |
| 4,972,154 | A * | 11/1990 | Bechtel | G01N 33/46 324/663 |
| 5,111,861 | A | 5/1992 | Gore et al. | |
| 5,257,101 | A | 10/1993 | Lee | |
| 5,412,220 | A | 5/1995 | Moore | |

(Continued)

FOREIGN PATENT DOCUMENTS

| | | | |
|---|---|---|---|
| CA | 2800409 | A1 | 7/2013 |
| WO | WO 90/11488 | | 10/1990 |

*Primary Examiner* — Mohammad J Rahman

(74) *Attorney, Agent, or Firm* — Stoel Rives LLP

(57) ABSTRACT

A lumber check grader-actuatable interface enables a check grader to interact with grade-quality measured boards of lumber conveyed along a flow path and passing in front of the check grader. The interface accurately and continuously tracks the location of each board in front of a check grader and tracks the location of the check grader's hands relative to the boards. Gestures can, therefore, be used for a selected board to perform additional actions, such as changing the grade or changing the trims. The interface enables a check grader to walk alongside and keep pace with a board of interest as it is transported and to provide feedback to the interface about a needed change for the board of interest. By knowing which board is of interest to a check grader, the interface can display additional information for only that board without overwhelming the check grader with non-stop information overload.

22 Claims, 10 Drawing Sheets

(56) References Cited

U.S. PATENT DOCUMENTS

| | | | | |
|---|---|---|---|---|
| 6,031,567 | A | 2/2000 | Johnson | |
| 6,122,065 | A | 9/2000 | Gauthier | |
| 6,272,437 | B1 * | 8/2001 | Woods | G01N 23/04<br>700/110 |
| 6,826,990 | B2 | 12/2004 | Olsen | |
| 7,004,329 | B2 | 2/2006 | Magnan | |
| 7,200,458 | B2 | 4/2007 | Carman et al. | |
| 7,426,422 | B2 | 9/2008 | Carman et al. | |
| 2003/0009258 | A1 | 1/2003 | Conry | |
| 2003/0178586 | A1 * | 9/2003 | Hubert | B07C 5/14<br>250/559.25 |
| 2004/0246473 | A1 | 12/2004 | Hermary et al. | |
| 2005/0021280 | A1 | 1/2005 | Woods et al. | |
| 2010/0141754 | A1 | 6/2010 | Hiraoka | |
| 2011/0050872 | A1 | 3/2011 | Harbert et al. | |
| 2013/0176419 | A1 | 7/2013 | Conry et al. | |
| 2014/0104579 | A1 | 4/2014 | Blomquist et al. | |

* cited by examiner

CHECK GRADER-ACTUATABLE INTERFACE FOR BOARD LUMBER SCANNING

COPYRIGHT NOTICE

© 2015 Lucidyne Technologies, Inc. A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR §1.71(d).

TECHNICAL FIELD

This disclosure relates to grading board lumber quality and, in particular, to a lumber check grader-actuatable interface that enables a check grader to interact with grade-quality measured boards of lumber conveyed along a flow path and passing in front of the check grader.

BACKGROUND INFORMATION

Lumber is graded by application of regional grading standards, for example, the American Lumber Standards, which are based on one or more of the structural integrity, shape, dimensions, and appearance of a board. These grades take into account the sizes and locations of defects, together with the slopes of grains, shape, and dimensions to predict one or more of the load-bearing capacities and acceptable appearance of the boards. (These attributes of the boards, together with grade and trim symbols, are hereafter referred to collectively as "board attribute information.") For several decades, board lumber scanning systems have projected onto boards and displayed on monitors board attribute information solutions including board feature and quality information. With the advent of low-cost projectors, large format televisions, and augmented reality devices, however, the possibilities for what data can be presented to check graders have increased. There is still, however, a limit to the amount of board attribute information a check grader can absorb in the short amount of time available to check a board transported on a conveyor.

It is not unusual for a check grader to roam several steps in either direction along a board conveyor to interact with a particular board of interest, but existing systems have no real time feedback capability indicating that the check grader is interacting with a specific board. Typically, the check grader can observe the solution computed by a board scanning system and then choose to override that solution by writing a mark on the board indicating that it is to be processed at a later time. The amount of board attribute information available to the check grader is, however, limited by time and space.

Existing systems can visually project the solution onto the boards for the check grader to see and effect a grade/trim override if necessary. If, in these existing systems, the check grader changes the position of a board transported by a moving conveyor, the solution overlay is projected in the wrong location, i.e., to a place where the board was, not to the place where the board has been moved.

SUMMARY OF THE DISCLOSURE

The disclosed check grader-actuatable interface overcomes the solution overlay displacement problem by accurately and continuously tracking the location of each board in front of a check grader and tracking the location of the check grader's hands relative to the boards. As such, gestures can be used for a selected board to perform additional actions, including but not limited to, changing the grade or changing the trims and to request additional board attribute information be projected onto the board, displayed on a nearby monitor, or rendered in an augmented reality device (such as Google Glass or Microsoft HoloLens) worn by the operator.

The check grader-actuatable interface functions among a check grader, the board lumber the check grader is inspecting, and the automated board grading machine the check grader is supplementing. By measuring where the boards are located and the location of the check grader, the interface creates an association between them that allows the check grader to interact with the board and the solution in a way never before possible.

For example, when the check grader touches a board of particular interest, more detailed information can be rendered (by one or more of a projector, television, augmented reality device) for the check grader to learn more about that particular board. With this additional information, the check grader can then make a more informed decision about whether to change one or both of the grade and trims. Although some existing systems use voice recognition to allow the check grader to change the grade/trim, the check grader is constrained to a specific location where boards are presented in a controlled manner, one at a time to the check grader. The disclosed interface enables the operator to walk alongside and keep pace with a board of interest as it is transported and to provide feedback to the interface about a needed change for the board of interest. By knowing which board is of interest to a check grader, the interface can display additional information for only that board without overwhelming the check grader with non-stop information overload.

Additional aspects and advantages will be apparent from the following detailed description of preferred embodiments, which proceeds with reference to the accompanying drawings.

BRIEF DESCRIPTION OF THE DRAWINGS

FIGS. 5-1, 5-2, 5-3, and 5-4 are images developed by sequential processing of a depth image signal output of the 3D depth camera shown in FIGS. 1A and 1B.

DETAILED DESCRIPTION OF PREFERRED EMBODIMENTS

Figure 1A:
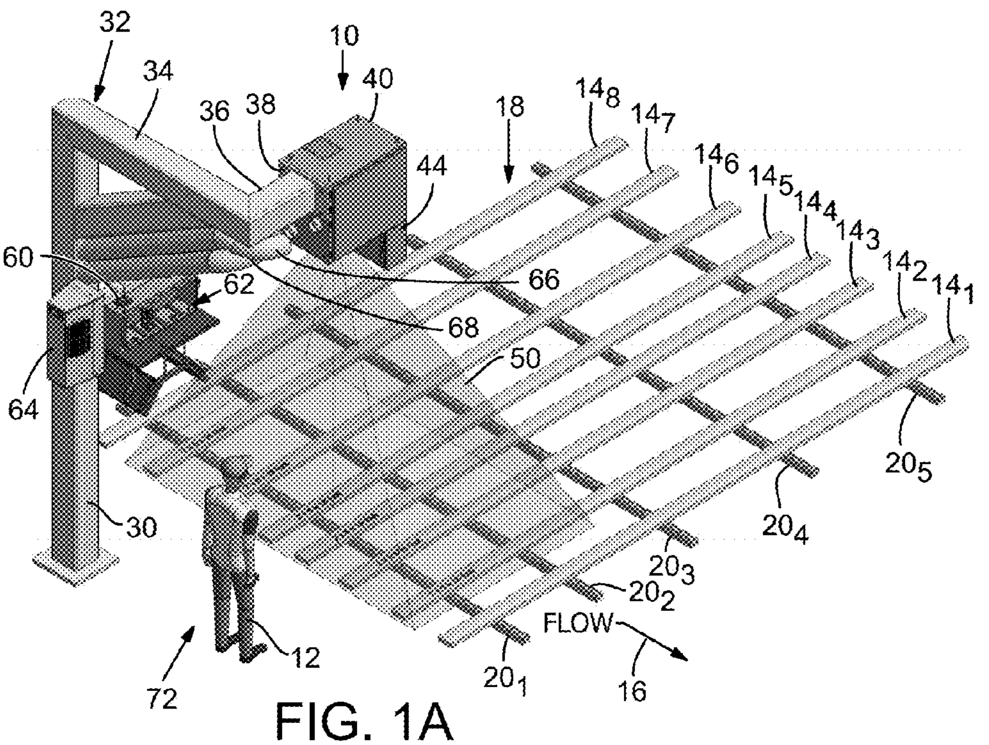
FIGS. 1A and 1B show from two different vantage points pictorial isometric views of a check grader-actuatable interface operating in a preferred embodiment in accordance with the present disclosure.
Figure 1B:
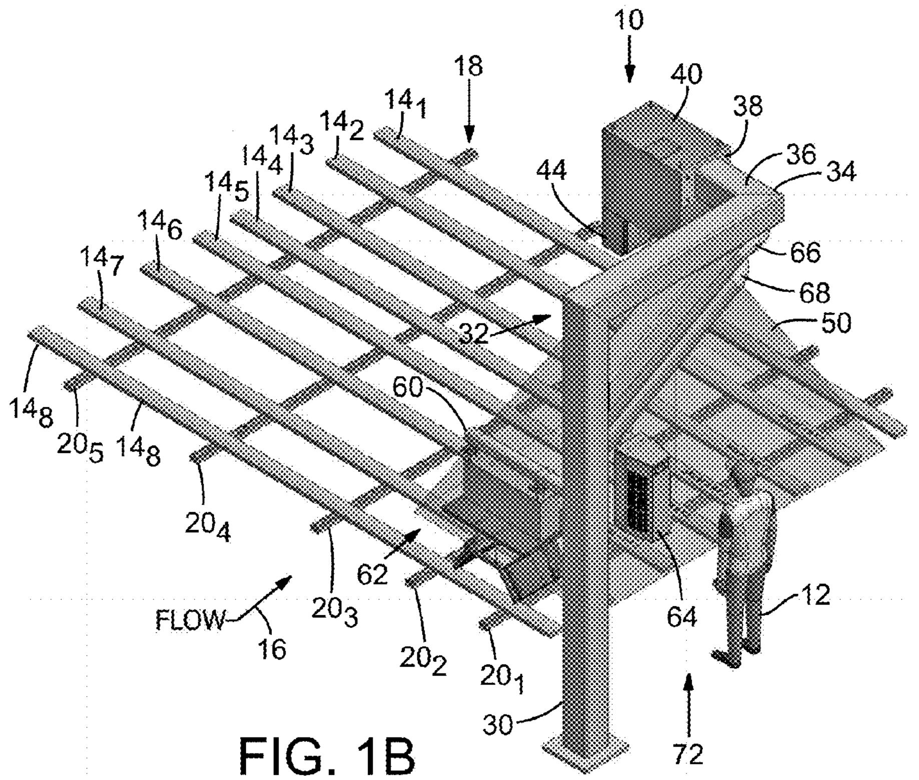

FIGS. 1A and 1B show from two different vantage points a check grader-actuatable interface 10 operating in a preferred embodiment in accordance with the present disclosure. With reference to FIGS. 1A and 1B, a check grader 12 inspects each one of eight grade-quality measured, generally parallel aligned boards $\mathbf{14}_1$, $\mathbf{14}_2$, $\mathbf{14}_3$, $\mathbf{14}_4$, $\mathbf{14}_5$, $\mathbf{14}_6$, $\mathbf{14}_7$, and $\mathbf{14}_8$ (collectively, "boards 14") transported along a board flow path 16 defined by a conveyor 18 formed of spaced-apart lug chains $\mathbf{20}_1$, $\mathbf{20}_2$, $\mathbf{20}_3$, $\mathbf{20}_4$, and $\mathbf{20}_5$ (collectively, "lug chains 20"). Check grader 12 can be a human grader, quality control inspector, machine operator observing equipment operation, operation supervisor, or any other individual interested in system operation. Boards 14 are set in a generally perpendicular orientation relative to the lengths of lug chains 20 as they move boards 14 along board flow path 16. There are no lane dividers separating, or upwardly projecting lugs maintaining a uniform parallel alignment of, adjacent boards 16 transported by conveyor 18.

Figure 2A:
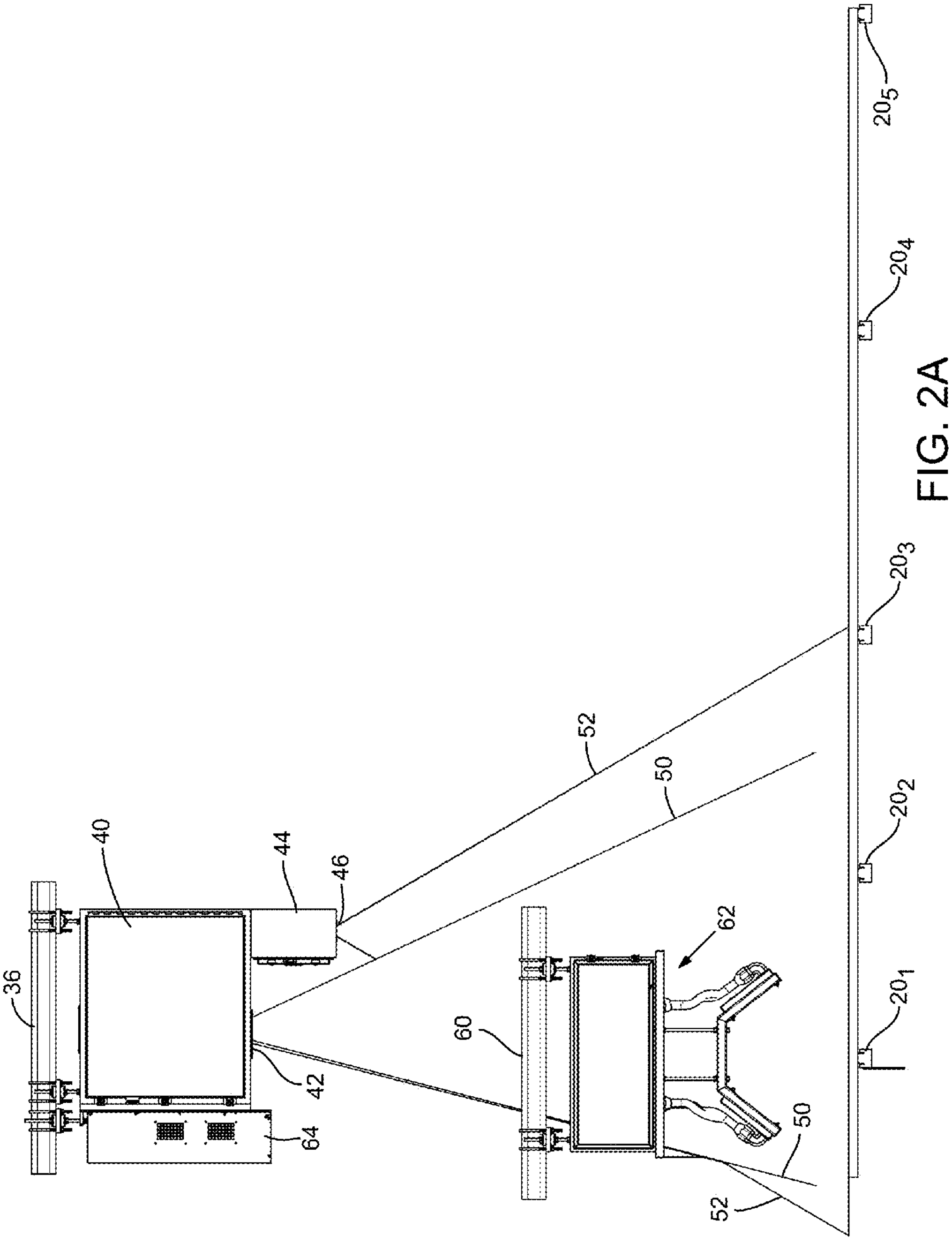
FIGS. 2A and 2B are diagrams showing in, respectively, the direction of a board flow path and the viewing direction of a check grader, the overlap of a field of view of an image projector and a field of view of a 3D depth camera shown in FIGS. 1A and 1B.
Figure 2B:
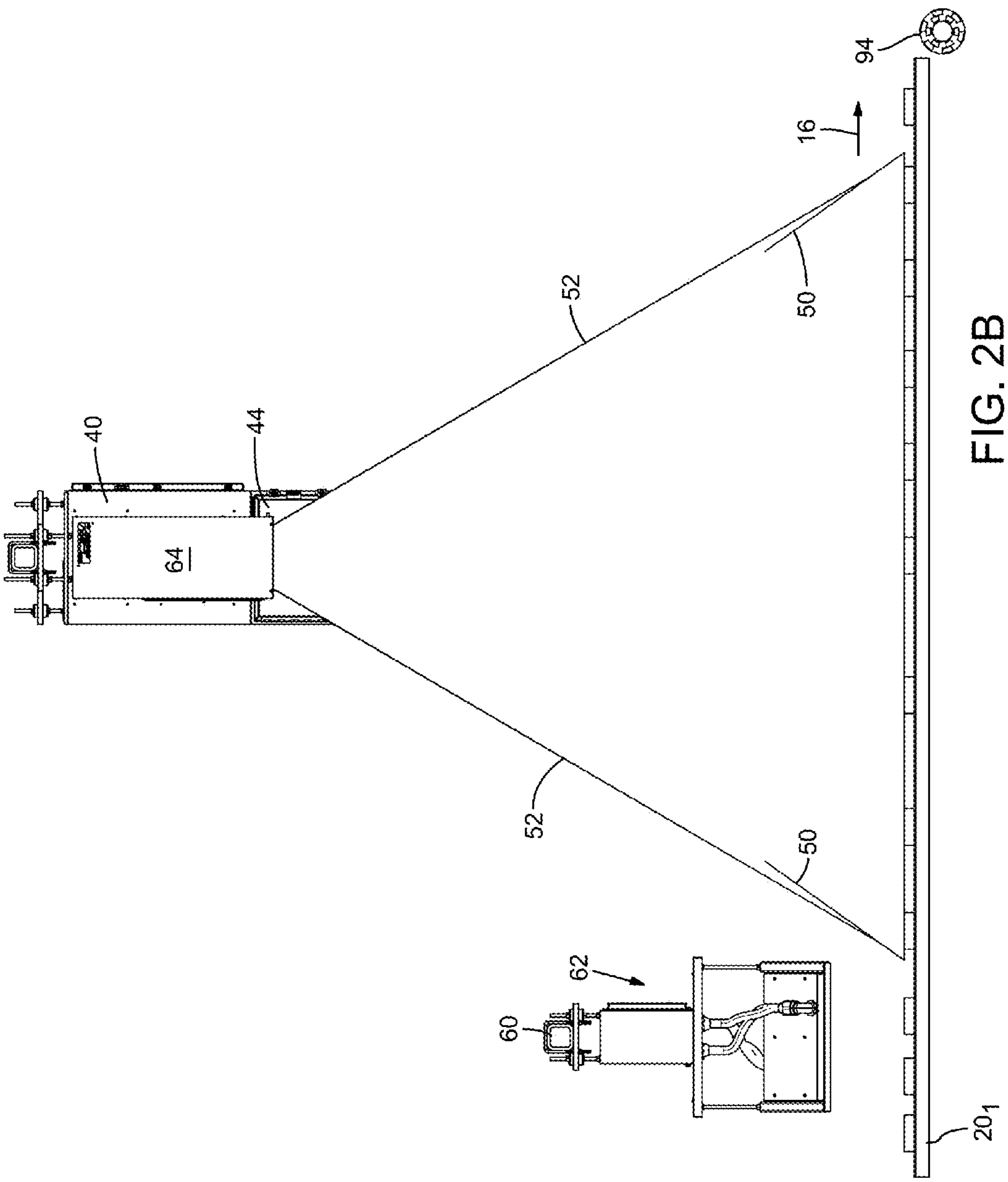
Figure 3:
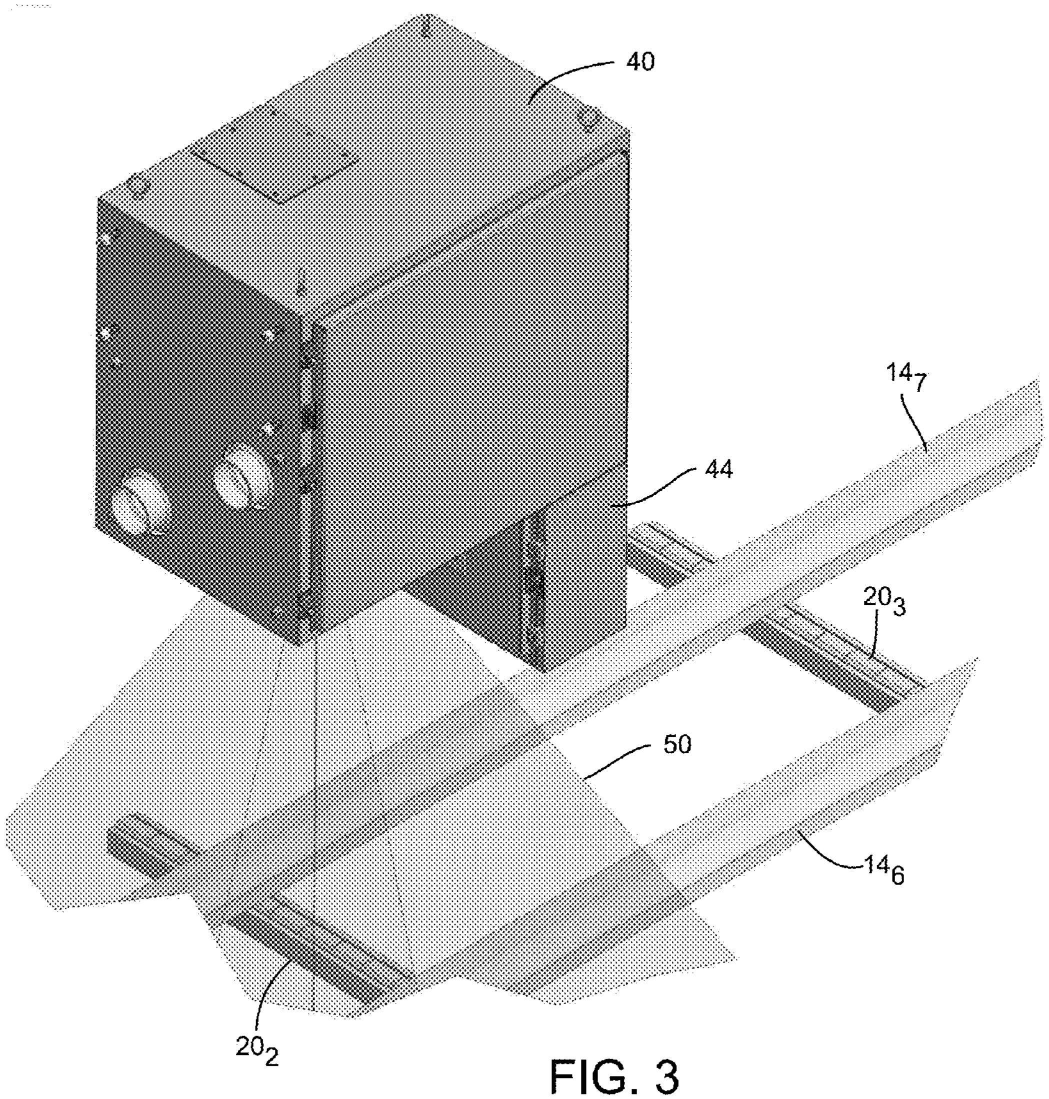
FIG. 3 is an enlarged fragmentary pictorial isometric view of enclosures for the image projector and 3D depth camera and of the field of view of the image projector shown in FIG. 1A.

An upright mounting member 30 supports at its top an L-shaped mounting arm 32 having a longer arm portion 34 extending along the lengths of lug chains 20 and a shorter arm portion 36 forming a right angle relative to arm portion 34 and extending in plane parallel relationship over boards 14 transported by conveyor 18. The free end of shorter arm portion 36 terminates in a mounting plate 38, to which is secured an enclosure 40 of an overhead image projector 42 (FIG. 2A). Enclosure 40 also houses a personal computer on which operate the image processing algorithms described below. An enclosure 44 of a three-dimensional depth camera ("3D depth camera") 46 (FIG. 2A) providing a depth image signal output to a board location tracking module 48 (FIG. 4) operating on the personal computer is affixed to enclosure 40 of image projector 42. Image projector 42 has a field of view 50, which, as shown in FIGS. 1A and 1B, covers about 7 ft. (2.13 m) down the length of boards $\mathbf{14}_2$, $\mathbf{14}_3$, $\mathbf{14}_4$, $\mathbf{14}_5$, $\mathbf{14}_6$, and $\mathbf{14}_7$ to project onto their surfaces images of one or more items of board attribute information, including grade symbols and trim symbols. The 3D depth camera 46 has a field of view 52. FIGS. 2A and 2B are diagrams showing, respectively, in the direction of board flow path 16 and in the viewing direction of check grader 12, the overlap of field of view 50 of image projector 42 and field of view 52 of 3D depth camera 46. With reference to FIGS. 2A and 2B, field of view 52 need not be the same size as that of field of view 50, but for practical reasons it is advantageous to have field of view 52 overlap field of view 50 as much as possible. FIG. 2A shows that field of view 52 spans farther in the direction transverse to board flow path 16 than does field of view 50. FIG. 2B shows that fields of view 50 and 52 span about the same distance in the direction of board flow path 16. FIG. 3 is an enlarged fragmentary view of enclosures 40 and 44 and field of view 50. The portion of conveyor 18 within field of view 50 is called a grading table.

Upright mounting member 30 supports along its length a mounting arm 60 from which suspends a board recognition system 62 positioned adjacent the upstream side of field of view 50. A preferred board recognition system 62 is a True-Q® board tracking system manufactured by Lucidyne Technologies, Inc., which is the assignee of this patent application. The True-Q® system is disclosed in U.S. Pat. Nos. 7,426,422 and 7,200,458 and, as described below, implements a board recognition method that uses a previously acquired fiberprint of each board to confirm its identification upon reaching lug chains 20.

A closed loop air conditioner 64 mounted to upright mounting member 30 propels cold air flow at 4000-5000 BTU/hr through an insulated inlet duct 66 and an insulated outlet duct 68 connected to enclosure 40 to maintain an acceptable temperature environment for the electrical and electronic equipment operating inside of it. (FIGS. 2A and 2B show a version of air conditioner 64 that is mounted directly onto enclosure 40, thereby eliminating the ductwork shown in FIGS. 1A and 1B.)

Check grader 12 stands in a check grader work space 72 to visually inspect boards 14 as they are transported downstream from board recognition system 62 and pass through field of view 50. Check grader work space 72 is defined as an area located generally outside of field of view 50 and adjacent lug chain $\mathbf{20}_1$ of the grading table. Check grader 12 standing in work space 72 performs one or both of two tasks. The first task is reading the board attribute information or symbols projected onto boards 14 on the grading table, and the second task is reaching into field of view 50 and manipulating or marking boards 14 on the grading table. FIGS. 1A and 1B show boards $\mathbf{14}_2$, $\mathbf{14}_3$, $\mathbf{14}_4$, $\mathbf{14}_5$, $\mathbf{14}_6$, and $\mathbf{14}_7$ lying on, board $\mathbf{14}_8$ positioned upstream of, and board $\mathbf{14}_1$ positioned downstream of, the grading table.

Figure 4:
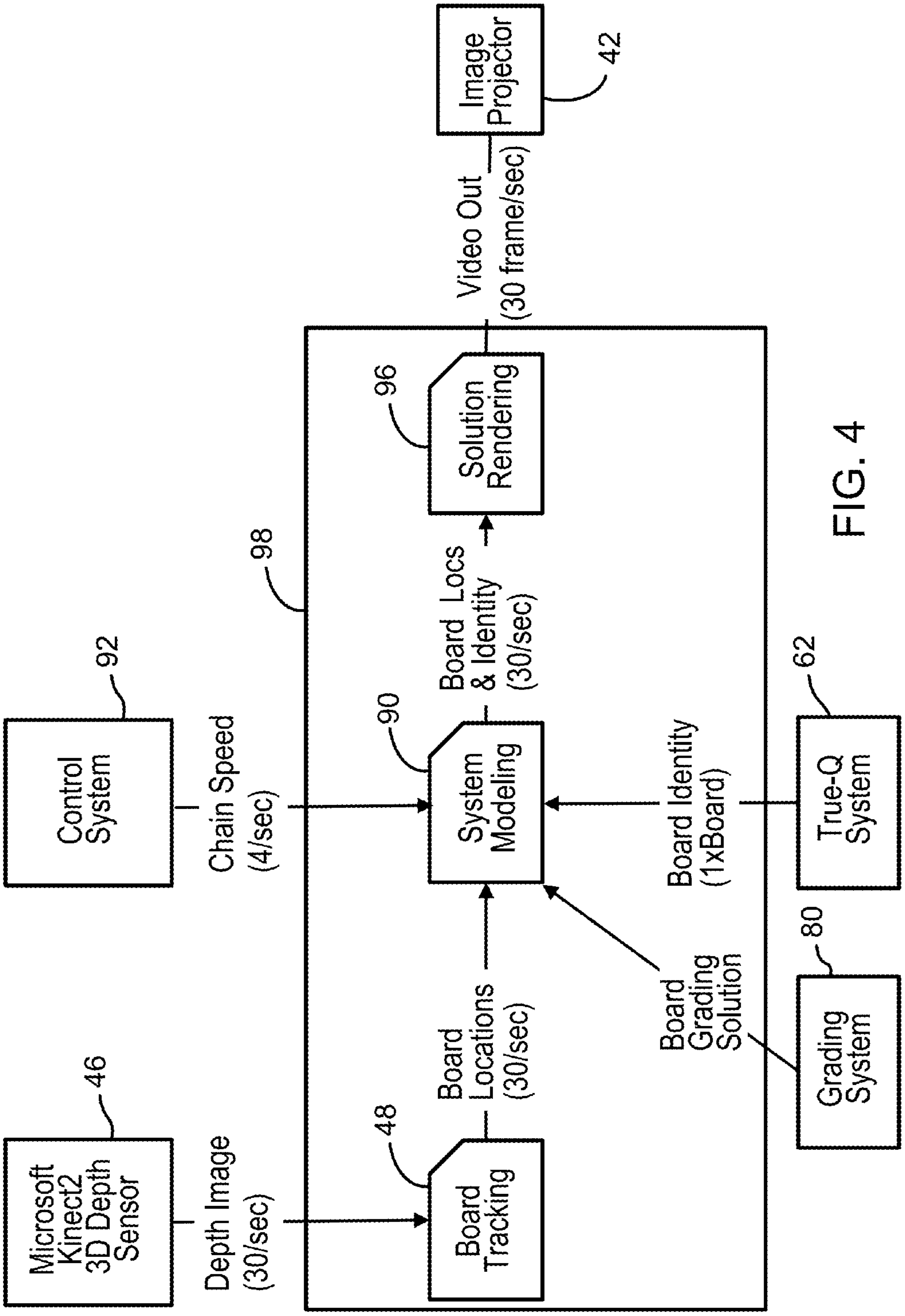
FIG. 4 is a block diagram of major sources of data and a personal computer contained in the image projector enclosure of the check grader-actuatable interface of FIGS. 1A and 1B.

FIG. 4 is a block diagram of the major sources of data and the information processing modules of check grader-actuatable interface 10. With reference to FIGS. 1A, 1B, and 4, before reaching board recognition system 62, boards 14 are scanned and assigned sequential board numbers that are used for all internal tracking and processing. A preferred board scanning system 80 (FIG. 4) performing these operations is a GradeScan® automated lumber scanner, which is manufactured by Lucidyne Technologies, Inc. Board scanning system 80 uses sensor technologies to detect defects in and other attributes of boards 14. Board scanning system 80 captures images on all four sides of each one of boards 14 and associates the four images of the board with its sequential board number. These image data, board attribute information including defect information, and the associated board number are stored in memory. The GradeScan® board scanning system 80 places no tracking symbols (e.g., ink, labels, and spray) on boards 14.

Boards 14 leaving board scanning system 80 are transported by an endless conveyor (not shown) to lug chains 20. Boards 14 transported between board scanning system 80 and lug chains 20 might become out of sequential order, or one of boards 14 might break and fail to reach lug chains 20. Board recognition system 62, which is positioned upstream of field of view 50, detects such re-ordering or absence of one of boards 14. Board recognition system 62 has a photoeye and an area camera, the photoeye detecting each one of incoming boards 14 and providing a trigger signal to which the area camera responds by capturing a single image of each one of boards 14 as they reach lug chains 20. Board recognition system 62 compares the single image with the images of the primary faces of the board captured by and stored in board scanning system 80 to confirm the identity of the board before it enters field of view 50. If the single image does not match the expected board, board recognition system 62 looks upstream and downstream at images of several boards 14 previously measured by board scanning system 80 in an attempt to find a match. Board recognition system 62 more heavily favors the closest boards 14.

Boards 14 leaving board recognition system 62 are transported into field of view 52 of 3D depth camera 46. A preferred three-dimensional depth camera is a Kinect2 sensor, manufactured by Microsoft® Corporation. The Kinect2 sensor is a physical device with depth sensing technology, a built-in color camera, an infrared (IR) emitter, and a microphone array, enabling it to sense the locations, movements, and voices of people. Board location tracking module 48 acquires at 30 frames/sec the depth image signal output of 3D depth camera 46.

FIGS. 5-1, 5-2, 5-3, and 5-4 are images developed by sequential processing of a depth image signal output of 3D depth camera 46.

Figures 1, 5:
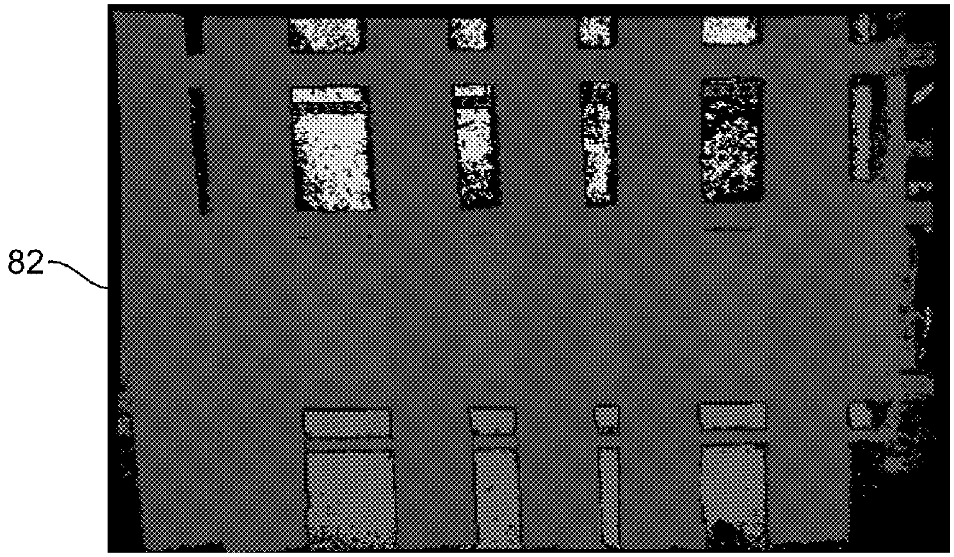

FIG. 5-1 shows a depth image acquired from 3D depth camera 46 by board location tracking module 48. Image 82 represents 6 ft.-8 ft. (1.83 m-2.44 m) of the ends of boards 14 nearer to check grader workspace 72.

Figures 2, 5:
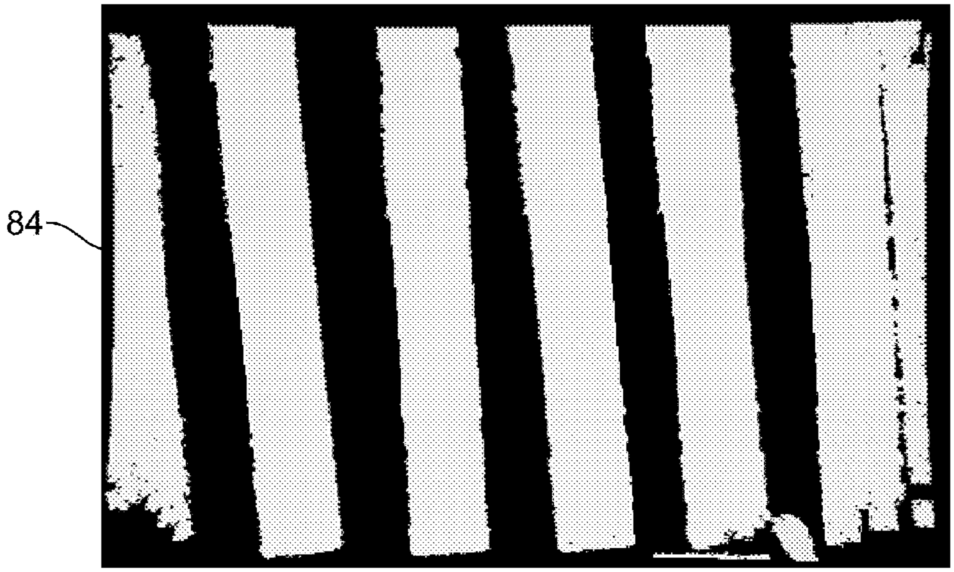
Figures 3, 5:
Figures 4, 5:
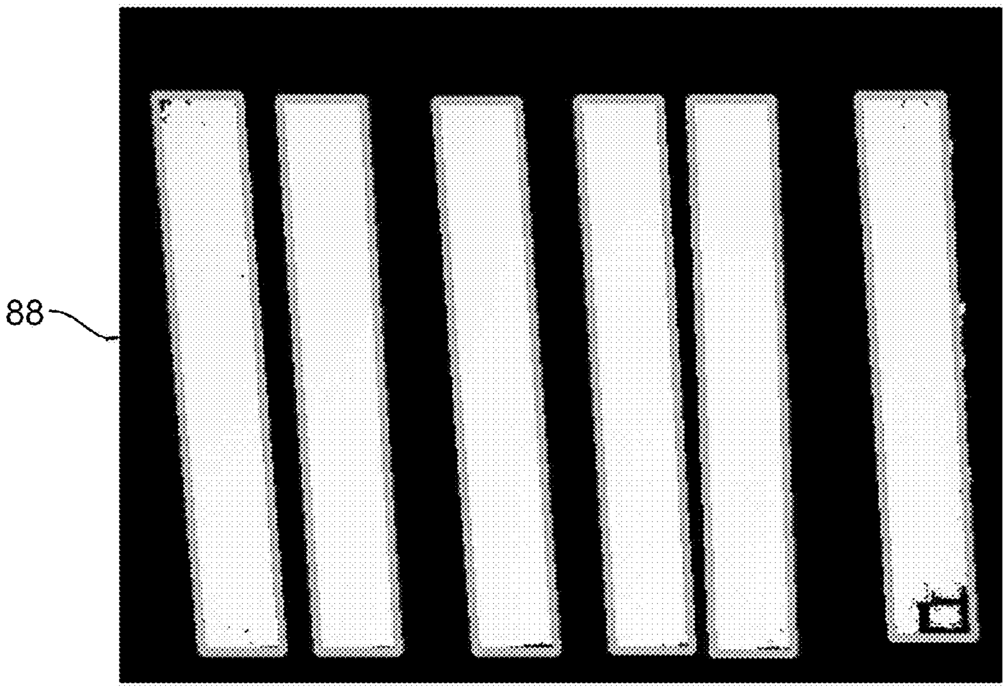

FIG. 5-2 shows a thresholded image 84 that is the result of application to image 82 of an image threshold algorithm masking all depth image information other than that of the top faces of boards 14. The image threshold algorithm can be any one of many well-known image threshold algorithms implemented in open source library software. The white regions of thresholded image 84 are categorized into blobs by application of software available from the Open Source Computer Vision (OpenCV) library of real-time computer vision programming functions. The blobs are filtered by size and shape; and blobs that are too small, wide, oblong, or excessively rotated in the plane of the board-carrying surface of conveyor 18 are discarded.

FIG. 5-3 shows an edge detected image 86 that is the result of vertical edge (both left and right) detection performed on the blobs. The vertical edges of each of the blobs are stored in a list of x, y coordinates.

FIG. 5-4 shows a board blob location image 88 that is the result of applying to image 86 a random sample consensus (RANSAC) line-fitting algorithm or any one of many well-known line-fitting algorithms implemented in open source library software. A line fit is performed on the left and right edge points of each blob. The left and right lines fitted for each blob are compared for parallelism and separation distance to confirm that the blob has parallel left and right edges (as does a board) and that the edges are about the same width apart as that of boards 14. The remaining left/right line pairs and associated blob bounds are assumed to be boards 14. At this stage of image processing, the locations but not the identities of boards 14 are known.

With reference to FIG. 4, a system modeling module 90 receives from board recognition system 62 board identity information for each one of boards 14 and from board scanning system 80 the defect information or "solution" associated with each one of boards 14. The solution includes a set of board attribute information, such as lumber grade, species of lumber, moisture content, grading solution, trimming solution, strength, shape, thickness, width, and identification number. The location, identity, and solution set of each of boards 14 are grouped together in a list of virtual boards formed in system modeling module 90.

A programmable logic controller ("PLC") 92 controls the movement of lug chains 20 and includes an encoder 94 (FIG. 2B) that produces a board conveyor movement signal indicating the speed of lug chains 20.

The speed of lug chains 20 is read periodically (e.g., 4 times/sec) from PLC 92 by system modeling module 90. The location of lug chains 20 is derived by interpolation from the speed values read between 0.25 second intervals. This approach to measuring expected speed and location is called the chain movement model. System modeling module 90 uses the periodic readings of the location of lug chains 20 to periodically "move" forward in space the virtual boards represented in FIG. 5-4. System modeling module 90 uses the well-known Kalman filter algorithm to create a balance between measured speed of lug chains 20 transporting boards 14 and the measured locations of boards 14 by board location tracking module 48 so as to minimize lag and jitter. If 3D depth camera 46 detects no hand gestures of check grader 12 on the board, the Kalman filter weights favor the chain movement model to compute the location of the board. If 3D depth camera 46 detects a hand of check grader 12 on the board, system modeling module 90 is programmed to expect that check grader 12 is going to physically move the board in an unpredictable fashion. In this case, board location tracking module 48 is favored over the chain movement model to measure the location of the board. The detection of hand gestures is described in detail below. System modeling module 90 periodically, i.e., 30 times/sec, receives board blob locations from board location tracking module 48. System modeling module 90 compares the virtual boards in the list to the blob locations and pairs the virtual boards with the blob locations based on how close they are. System modeling module 90 then micro-adjusts the board locations and orientations to match what board location tracking module 48 is detecting. This operation of system modeling module 90 allows check grader 12 to displace boards 14 and thereby change their locations and angles, and the virtual board locations remain properly tracked with the actual boards 14.

As described above, each one of boards 14 enters the grading table, and board location tracking module 48 reads the location of that board. As the board moves down the grading table, board location tracking module 48 continuously tracks the location of that board (and all other previous boards 14). If check grader 12 reaches out and touches a specific one of boards 14, 3D depth camera 46 detects that interaction. (Check grader 12 touching a board essentially always displaces the board from its original orientation on lug chains 20.) Any inputs to interface 10 from the check grader 12 can now be associated with that board. These inputs could be, but are not limited to, additional hand gestures, to which 3D depth camera 46 is responsive; oral statements via microphone; or pressing of buttons on an input device.

With respect to detection of hand gestures of check grader 12, system modeling module 90 computes a high/low gesture zone and a left/right gesture zone. High/low gesture zone extends a fixed first distance, e.g., 2 ft. (0.61 m), along the length of a board from its end nearer to check grader workspace 72, and left/right gesture zone extends a fixed second distance, e.g., 6 in. (15.24 cm), along the width of the board in the direction of board flow path 16. System modeling module 90 establishes a reference depth by computing an average depth of the top surface of the board and average depths at the left- and right-hand sides of the board. This computation can be performed with use of any one of well-known algorithms.

Whenever 3D depth camera 46 detects a depth of the high/low gesture zone that differs from the reference depth, this condition indicates that a hand of check grader 12 has reached into that gesture zone. Since the depth of the gesture zone is known, system modeling module 90 can detect whether the hand of check grader 12 is in contact with or above the surface of the board.

Whenever 3D depth camera 46 detects a depth of the left/right gesture zone that differs from the average depths, this condition indicates that a hand of check grader 12 has been placed at the left-hand side of the board, if the depth of the left gesture zone has changed, or at the right-hand side of the board, if the depth of the right gesture zone has changed.

Establishing left/right and high/low gesture zones provides eight unique combinations of detectable gestures. These gestures made by check grader 12 include placing the left hand above or on the board surface, right hand above or on the board surface, left hand on the left-hand side of the board, right hand on the right-hand side of the board, left hand above the board surface and the right hand on the right-hand side of the board, and right hand above the board surface and the left hand on the left-hand side of the board.

System modeling module 90 is programmable to deliver to a solution rendering module 96 a complete set or a subset of the set of board attribute information in response to a specific gesture made by check grader 12. Board location tracking module 48, system modeling module 90, and solution rendering module 96 operate on processor circuitry of the personal computer contained in enclosure 40. A rectangular block 98 containing modules 48, 90, and 96 in FIG. 4 represents the personal computer.

Figure 6A:
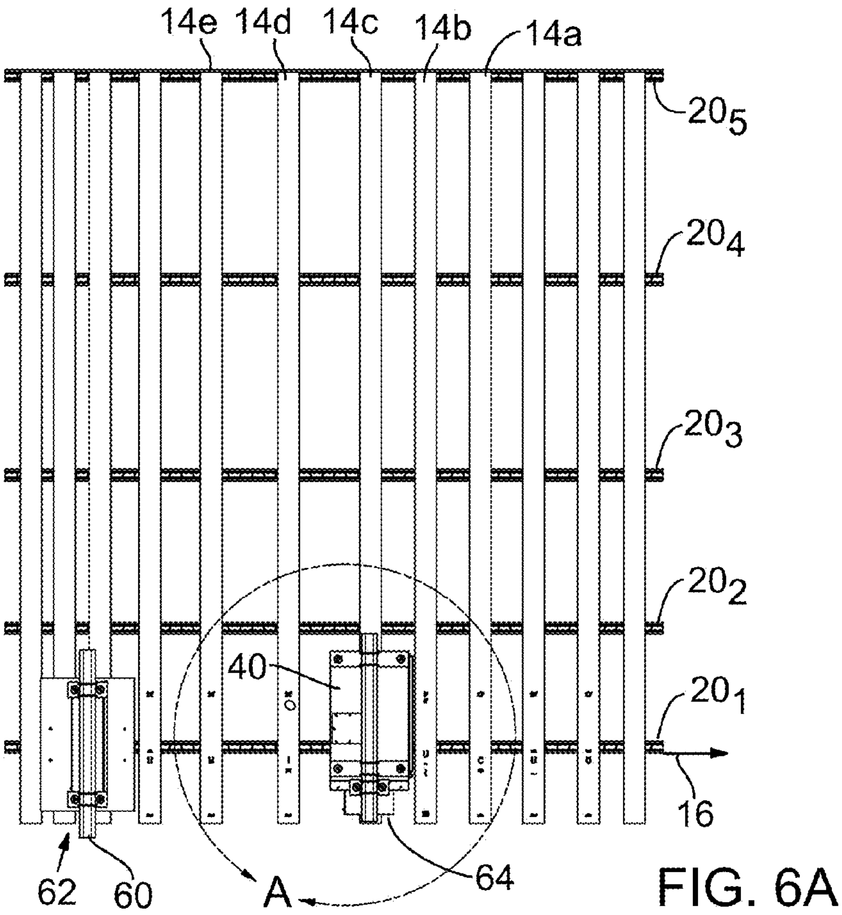
FIG. 6A is a diagram showing a top plan view of a group of twelve grade-quality measured boards transported along a board flow path.
Figure 6B:
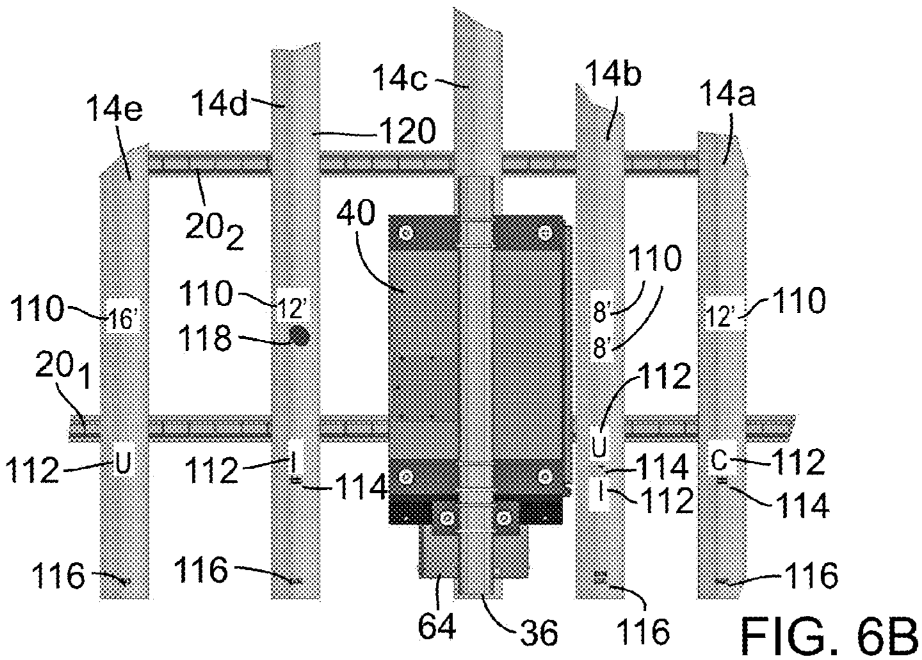
FIG. 6B is an enlarged fragmentary pictorial isometric view of five boards enclosed by a circle A drawn on FIG. 6A to identify a region within the field of view of the image projector and proximal to a check grader workspace.

For example, under nominal operating conditions, check grader 12 does not touch a board that check grader 12 concludes has the proper lumber grade projected onto the board surface. This nominal operating condition is illustrated in FIGS. 6A and 6B. FIG. 6A is a diagram showing a top plan view of a group of twelve grade-quality measured, generally parallel aligned boards 14 transported along board flow path 16. The three left-most and the one right-most boards 14 are outside of field of view 50 and, therefore, have no grade mark symbols or other board attribute information projected onto their top surfaces. FIG. 6B is an enlarged fragmentary view of boards 14*a*, 14*b*, 14*c*, 14*d*, and 14*e* enclosed by circle A drawn on FIG. 6A to identify a region within field of view 50 of image projector 42 and proximal to check grader workspace 72. Boards 14*a*, 14*b*, 14*d*, and 14*e* show projected on their top surfaces board length symbols 110, grade mark symbols 112, trim symbols 114, and board identification numbers 116. Board 14*b* shows two board length symbols 110 and two grade mark symbols 112 because board 14*b* is to be cut into two-8 ft lengths as indicated. Board 14*d* has a knot defect 118, and any board attribute information projected onto board 14*c* is obscured in FIGS. 6A and 6B by enclosure 40 and air conditioner 64.

Figure 7A:
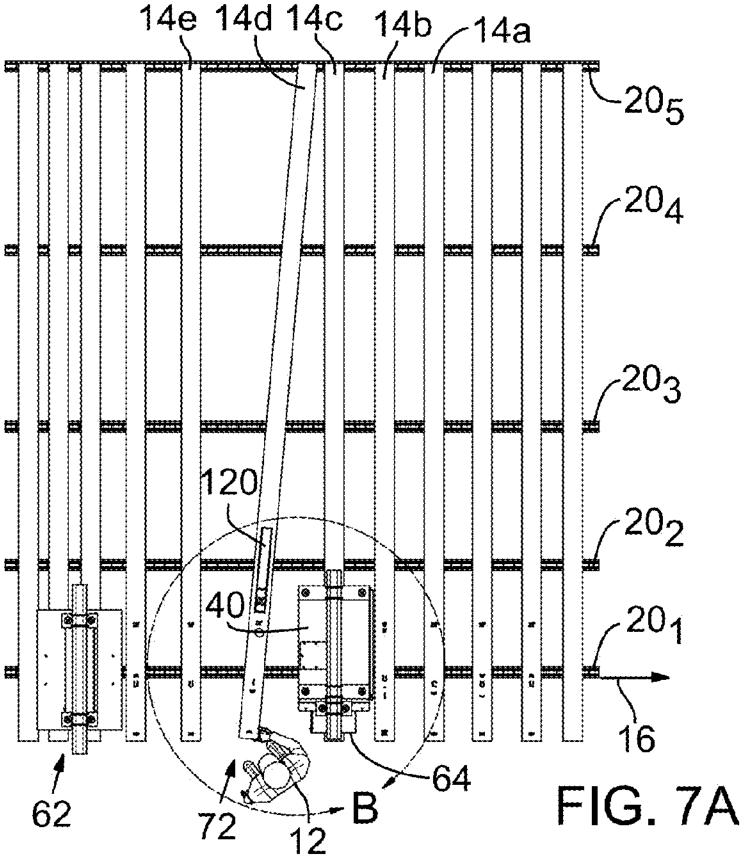
FIGS. 7A and 7B are reproductions of FIGS. 6A and 6B, respectively, with exception that FIGS. 7A and 7B show one of the five boards displaced from its original spatial alignment relative to adjacent boards.
Figure 7B:
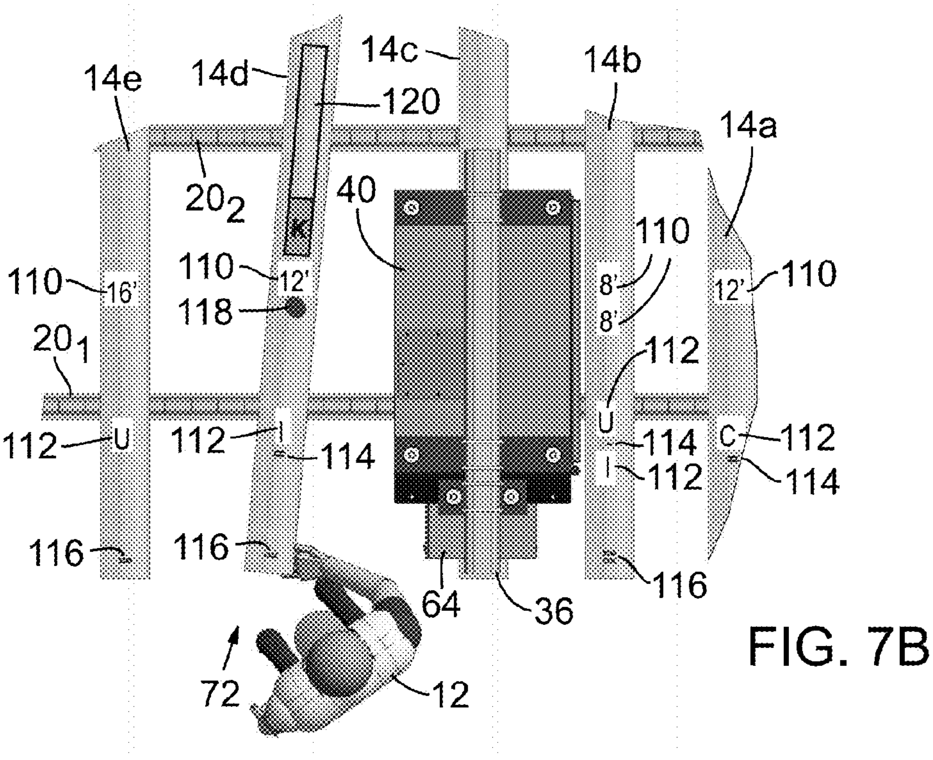

If upon inspection check grader 12 concludes that a board has projected on its surface board attribute information that was erroneously computed by board scanning system 80, check grader 12 touches the surface of the board. The operating condition resulting from the touching of a board by check grader 12 is illustrated in FIGS. 7A and 7B. FIG. 7A differs from FIG. 6A in that a circle B replaces circle A of FIG. 6A to show check grader 12 moving board 14*d* and a consequent projection of additional board attribute information 120 onto the top surface of board 14*d*. FIGS. 7A and 6A are otherwise the same. FIG. 7B is an enlarged fragmentary view of boards 14*a*, 14*b*, 14*c*, 14*d*, and 14*e* and of check grader 12 enclosed by circle B.

The detection by board location tracking module 48 and system modeling module 90 of the hand of check grader 12 touching board 14*d* causes delivery to solution rendering module 94 board attribute information 120 that would be useful for check grader 12 to know. FIGS. 7A and 7B illustrate board attribute information 120 as an image of a rectangle representing a small scale rendering of board 14*d*, in which rectangle a smaller shaded area marked with "K" indicates a portion of board 14*d* spoiled by knot 118. Board 14*d* is shown displaced from its original generally parallel spatial alignment with adjacent boards 14*e* and 14*c* shown in FIGS. 6A and 6B. Board attribute 120 is a member of a subset of board attribute information that is different from the subset of board attribute information shown in FIGS. 6A and 6B before the displacement of board 14*d*. The output of solution rendering module 96 is a 30 frames/sec stream of video, which is delivered to image projector 42. System modeling module 90 provides the different subset of solution information for projection onto the surface of the board. Board location tracking module 48 continuously monitors the location and orientation of each board; therefore, check grader 12 displacing board 14*d* to inspect it sees the projected information 110, 112, 114, 116, and 120 remain spatially aligned on the top surface of displaced board 14*d* as a consequence of the above-described adjustments made by system modeling module 90. This continuous monitoring enables check grader 12 to walk at a pace that permits observation of the projected information as lug chains 20 transport board 14*d*.

In the preferred embodiment described above, image projector 42 is the image display device that receives the set or subset of board attribute information from solution rendering module 96. First and second alternative image display devices include, respectively, a large format display screen and an augmented reality device. Each of the first and second alternative image display devices displays to an observer a rendering of a subset of the set of board attribute information in spatial alignment with renderings of images of virtual boards produced in accordance with the operation of board location tracking module 48 or captured by the color camera of 3D depth camera 46. The above-described operation of system modeling module 90 maintains spatial alignment between the rendering of board attribute information and renderings of images of a displaced selected grade-quality measured board transported on lug chains 20.

Figure 8D:
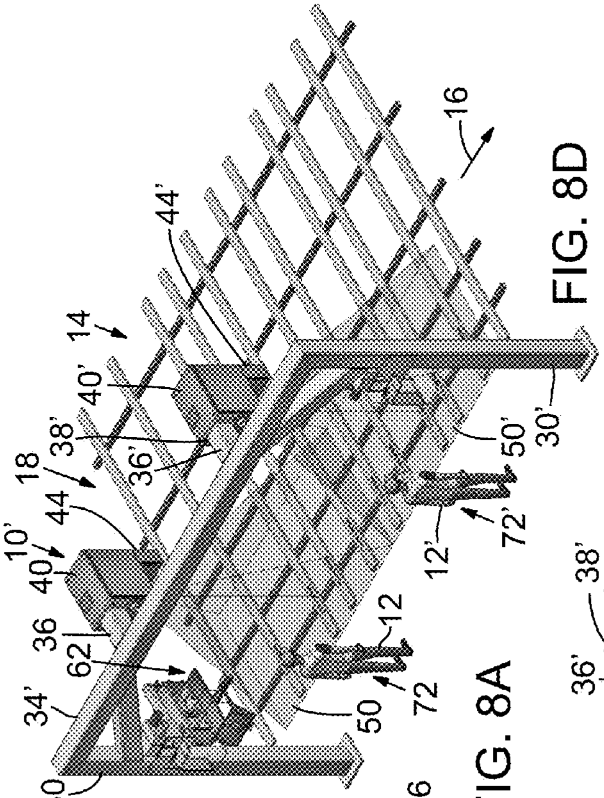
FIGS. 8A, 8B, 8C, and 8D are, respectively, top plan, side elevation, end (upstream-directed), and pictorial isometric views of an embodiment of the disclosed check grader-actuatable interface constructed with two check grader workspaces.
Figure 8A:
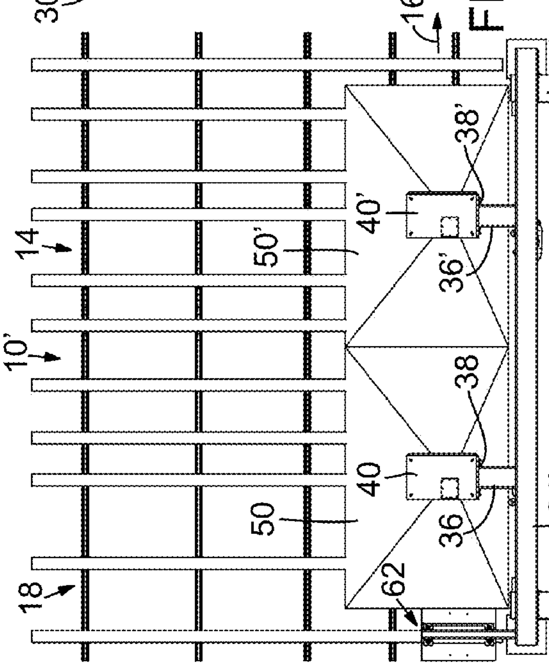
Figure 8C:
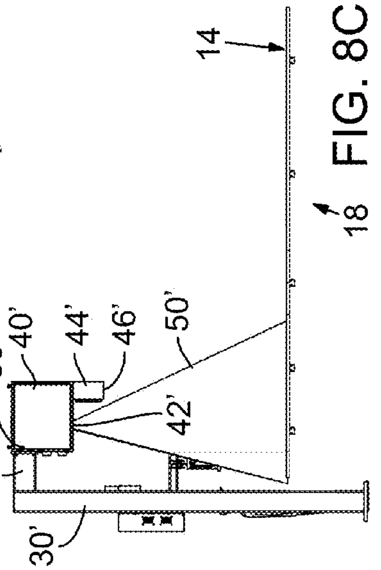
Figure 8B:
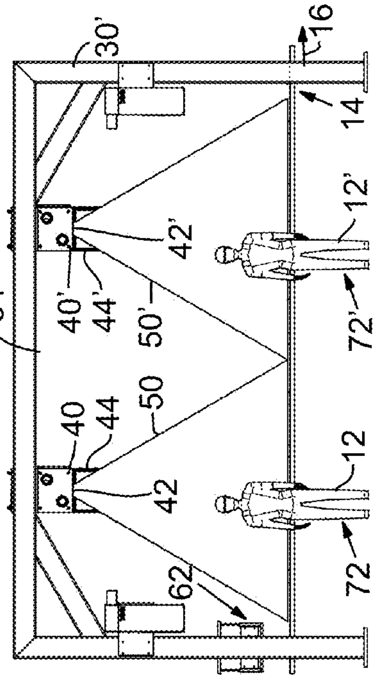

FIGS. 8A, 8B, and 8C are diagrams and FIG. 8D is a pictorial view of an embodiment of the disclosed check grader-actuatable interface 10' constructed for simultaneous use by two check graders 12 and 12' standing at respective check grader workspaces 72 and 72'. With reference to FIGS. 8A, 8B, 8C, and 8D, check grader-actuatable interface 10' constitutes an expanded version of check grader-actuatable interface 10, by addition of a second enclosure 40' of a second overhead image projector 42' and a second enclosure 44' of a second 3D depth camera 46'. Enclosure 40' contains a personal computer having processor circuitry on which board tracking, system modeling, and solution rendering modules operate as described above for check grader-actuatable interface 10.

Upright mounting member 30 and an upright mounting member 30' support at their top ends a beam 34' to form an inverted U-shaped structure. Arm portion 36 terminating in mounting plate 38 and an arm portion 36' terminating in a mounting plate 38' extend from beam 34' and support enclosures 44 and 44', respectively. FIG. 8D shows field of view 50 of image projector 42 covering four boards 14 in front of check grader 12 and a field of view 50' of image projector 42' covering five boards 14 in front of check grader 12'. Check graders 12 and 12' may coordinate their inspection activities in any number of ways such as, for example, check graders 12 and 12' alternating inspections of boards 14 as they are transported by conveyor 18 along board flow path 16 through check grader-actuatable interface 10'.

It will be obvious to those having skill in the art that many changes may be made to the details of the above-described embodiments without departing from the underlying principles of the invention. The scope of the present invention should, therefore, be determined only by the following claims.

The invention claimed is:

1. A method of facilitating check grader interaction by physical contact with grade-quality measured boards of lumber as they are transported along a lumber flow path, comprising:

transporting multiple grade-quality measured boards of lumber on a conveyor and along a board flow path, each of the multiple grade-quality measured boards characterized by a set of board attribute information and associated board identification information that are stored in memory;

obtaining a board conveyor movement signal representing expected movement of the multiple grade-quality measured boards transported on the conveyor;

identifying the multiple grade-quality measured boards transported on the conveyor;

processing the identified multiple grade-quality measured boards by a check grader interface system that includes a three-dimensional depth camera, an image display device, a board location tracking module, and a system modeling module, the three-dimensional depth camera acquiring area-depth images of the identified multiple grade-quality measured boards as they are transported through a field of view associated with the image display device, the image display device displaying a rendering of a subset of the set of board attribute information in spatial alignment with the identified multiple grade-quality measured boards as they are transported through the field of view, and the board location tracking module using the area-depth images and the board conveyor movement signal to produce board location tracking signals representing locations of the identified multiple grade-quality measured boards as they are transported through the field of view;

defining, in proximity to the conveyor, a check grader space from which a check grader can displace a selected one of the identified multiple grade-quality measured boards transported through the field of view; and processing by operation of the system modeling module, in response to displacement by check grader tactile contact with the selected one of the identified multiple grade-quality measured boards, the board location tracking signals to display the rendering of the subset or to display a rendering of a different subset of the set of board attribute information in spatial alignment with the displaced selected identified grade-quality measured board.

2. The method of claim 1, in which the multiple grade-quality measured boards of lumber include grade-quality scanned boards of lumber.

3. The method of claim 1, in which no divider separates mutually adjacent boards of the multiple grade-quality measured boards transported on the conveyor.

4. The method of claim 1, in which the three-dimensional depth camera produces a depth image output signal from which the board location tracking module periodically acquires depth images of the identified multiple grade-quality measured boards captured by the three-dimensional depth camera, the board location tracking module processing the depth images to produce image blobs representing locations of the identified multiple grade-quality measured boards on the conveyor.

5. The method of claim 4, further comprising using an area camera to capture images of surface areas of the identified multiple grade-quality measured boards, the area camera included in a board recognition system that is operable to access the board identification information, and in which the system modeling module correlates the image blobs and the board identification information to associate the image blobs of the identified multiple grade-quality measured boards and their associated board identification information, and in which the system modeling module correlates the set of board attribute information and the corresponding selected one of the grade-quality measured boards so that the image display device displays the rendering of the subset of the set of board attribute information in spatial alignment with the selected one of the grade-quality measured boards.

6. The method of claim 1, in which the selected one of the multiple grade-quality measured boards has a length that defines a longitudinal axis, and in which the displacement entails the check grader rotating the selected one of the multiple grade-quality measured boards about the longitudinal axis.

7. The method of claim 6, in which the image display device displaying a rendering of a subset of the set of board attribute information in spatial alignment with the identified multiple grade-quality measured boards includes an image projector projecting a rendering of a subset of the set of board attribute information onto surfaces of the identified multiple grade-quality measured boards as they are transported through the field of view, and in which the processing by the system modeling module causes the board location tracking signals to project the rendering of the subset or to project a rendering of a different subset of the set of board attribute information onto, and in spatial alignment with, the surface of the displaced selected one of the multiple grade-quality measured boards.

8. The method of claim 1, in which the board conveyor movement signal is obtained from an encoder positioned in operative association with the conveyor.

9. A method of facilitating check grader interaction with grade-quality measured boards of lumber as they are transported along a lumber flow path, comprising:

transporting multiple grade-quality measured boards of lumber on a conveyor and along a board flow path, each of the multiple grade-quality measured boards characterized by a set of board attribute information and associated board identification information that are stored in memory;

obtaining a board conveyor movement signal representing expected movement of the multiple grade-quality measured boards transported on the conveyor;

identifying the multiple grade-quality measured boards transported on the conveyor;

processing the identified multiple grade-quality measured boards by a check grader interface system that includes a three-dimensional depth camera, an image display device, a board location tracking module, and a system modeling module, the three-dimensional depth camera acquiring area-depth images of the identified multiple grade-quality measured boards as they are transported through a field of view associated with the image display device, the image display device displaying a rendering of a subset of the set of board attribute information relating to the identified multiple grade-quality measured boards as they are transported through the field of view, and the board location tracking module using the area-depth images and the board conveyor movement signal to produce board location tracking signals representing locations of the identified multiple grade-quality measured boards as they are transported through the field of view;

defining, in proximity to the conveyor, a check grader space from which a check grader can interact with a selected one of the identified multiple grade-quality measured boards transported through the field of view; and processing by operation of the system modeling module, in response to check grader interaction with the selected one of the identified multiple grade-quality measured boards, the board location tracking signals to display a rendering of a different subset of the set of board attribute information relating to the selected identified grade-quality measured board.

10. The method of claim 9, in which no divider separates mutually adjacent boards of the multiple grade-quality measured boards transported on the conveyor.

11. The method of claim 9, in which the three-dimensional depth camera produces a depth image output signal from which the board location tracking module periodically acquires depth images of the identified multiple grade-quality measured boards captured by the three-dimensional depth camera, the board location tracking module processing the depth images to produce image blobs representing locations of the identified multiple grade-quality measured boards on the conveyor.

12. The method of claim 11, further comprising using an area camera to capture images of surface areas of the identified multiple grade-quality measured boards, the area camera included in a board recognition system that is operable to access the board identification information, and in which the system modeling module correlates the image blobs and the board identification information to associate the image blobs of the identified multiple grade-quality measured boards and their associated board identification information, and in which the system modeling module correlates the set of board attribute information and the corresponding selected one of the grade-quality measured boards so that the image display device displays the rendering of a different subset of the set of board attribute information relating to the selected grade-quality measured board.

13. The method of claim 9, in which the image display device displaying a rendering of a subset of the set of board attribute information relating to the identified multiple grade-quality measured boards includes an image projector projecting a rendering of a subset of the set of board attribute information onto surfaces of the identified multiple grade-quality measured boards as they are transported through the field of view, and in which the processing by the system modeling module causes the board location tracking signals to project the rendering of a different subset of the set of board attribute information onto the surface of the selected grade-quality measured board.

14. A board lumber processing system, comprising:

a board scanning system implemented to analyze board lumber and provide multiple grade-quality measured boards, each of which characterized by a set of board attribute information and associated board identification information;

a conveyor constructed to transport the multiple grade-quality measured boards along a board flow path;

a conveyor movement detector providing a board conveyor movement signal representing expected movement of the multiple grade-quality measured boards transported on the conveyor;

a three-dimensional depth camera and an image display device having a field of view, the three-dimensional depth camera acquiring area-depth images of the multiple grade-quality measured boards as they are transported through the field of view of the image display device; and a board location tracking module and a system modeling module operating on processor circuitry, the board location tracking module using the area-depth images and the board conveyor movement signal to produce board location tracking signals representing locations and orientations of the multiple grade-quality measured boards transported through the field of view of the image display device, and the system modeling module, in response to detection by the three-dimensional depth camera of touching of one of the multiple grade-quality measured boards by a check grader, performing adjustments so that the locations and orientations of the multiple grade-quality measured boards represented by the board location tracking signals match the locations and orientations of the multiple grade-quality measured boards detected by the board location tracking module, thereby to cause the image display device to display a rendering of a subset of the set of board attribute information in spatial alignment with the multiple grade-quality measured boards as they are transported through the field of view of the image display device.

15. The system of claim 14, further comprising a board recognition system positioned upstream of the three-dimensional depth camera along the board flow path to confirm the identification of the multiple grade-quality measured boards transported on the conveyor downstream from the board scanning system.

16. The system of claim 14, in which no divider separates mutually adjacent boards of the multiple grade-quality measured boards transported on the conveyor.

17. The system of claim 14, in which the three-dimensional depth camera produces a depth image output signal from which the board location tracking module periodically acquires depth images of the multiple grade-quality measured boards captured by the three-dimensional depth camera, the board location tracking module processing the depth images to produce image blobs representing locations of the multiple grade-quality measured boards on the conveyor.

18. The system of claim 14, in which the image display device includes an image projector projecting a rendering of a subset of the set of board attribute information onto surfaces of the multiple grade-quality measured boards as they are transported through the field of view of the image projector.

19. The system of claim 14, in which the image display device includes a display screen that displays a rendering of a subset of the set of board attribute information in spatial alignment with renderings of images of virtual boards.

20. The system of claim 14, in which the image display device includes an augmented reality device that displays a rendering of a subset of the set of board attribute information in spatial alignment with renderings of images of virtual boards.

21. The method of claim 1, further comprising the system modeling module computing a reference depth of, and a gesture zone defining a gesture zone depth associated with, the displaced selected identified grade-quality measured board, and in which the three-dimensional depth camera determines an occurrence of the check grader contact with the selected one of the identified multiple grade-quality measured boards by detecting a difference between the gesture zone depth and the reference depth, the difference indicating whether the check grader is reaching into the gesture zone and physically contacting the selected one Of the identified multiple grade-quality measured boards.

22. The method of claim 1, in which the conveyor defines a surface of a plane, and in which the displacement entails the check grader moving the selected one of the multiple grade-quality measured boards in the planar surface of the conveyor.

* * * * *